United States Patent
Sullivan et al.

(10) Patent No.: US 6,208,895 B1
(45) Date of Patent: Mar. 27, 2001

(54) CIRCUIT FOR PERFORMING EXTERNAL PACING AND BIPHASIC DEFIBRILLATION

(75) Inventors: Joseph L. Sullivan; Richard C. Nova; Lawrence A. Borschowa, all of Kirkland, WA (US)

(73) Assignee: Physio-Control Manufacturing Corporation, Redmond, WA (US)

(*) Notice: Subject to any disclaimer, the term of this patent is extended or adjusted under 35 U.S.C. 154(b) by 0 days.

(21) Appl. No.: 09/172,322

(22) Filed: Oct. 13, 1998

(51) Int. Cl.$^7$ ........................................... A61N 1/39
(52) U.S. Cl. ........................................... 607/4
(58) Field of Search .................. 607/4, 9, 74, 5

(56) References Cited

U.S. PATENT DOCUMENTS

| | | | |
|---|---|---|---|
| 4,402,322 | * | 9/1983 | Duggan ..................... 607/9 |
| 4,693,253 | * | 9/1987 | Adams ..................... 607/4 |

* cited by examiner

Primary Examiner—Kennedy Schaetzle

(74) Attorney, Agent, or Firm—Christensen O'Connor Johnson Kindness PLLC

(57) ABSTRACT

An external defibrillator/pacer (8) includes an output circuit (14) with four legs arrayed to form an H-bridge coupled to an energy storage capacitor. The energy storage capacitor delivers an external defibrillation pulse with stored energy during a defibrillation mode and an external pacing pulse during a pacing mode. Each leg of the output circuit contains a switch (SW1–SW4). In a defibrillation mode, pairs of switches in the H-bridge are selectively switched to generate a biphasic defibrillation pulse. Three switches (SW1, SW3, SW4) are silicon controlled rectifiers (SCRs). Gate drive circuits (51, 53, 54) are coupled to the SCRs to bias the SCRs with a voltage that allows the SCRs in response to control signals. One switch (SW2) includes an insulated gate bipolar transistor (IGBT). A gate drive circuit (52) is coupled to the gate of the IGBTs to provide a slow turn-on and a fast turn-off of the IGBT. In a pacing mode, a bypass circuit or current source circuit is used to provide a current path bypassing an SCR switch (SW3), which cannot be triggered by the relatively low current of pacing pulses. One of the SCRs (SW4) may be replaced with an IGBT to allow generation of the pacing pulse with opposite polarity of the first phase of the defibrillation pulse.

33 Claims, 8 Drawing Sheets

CIRCUIT FOR PERFORMING EXTERNAL PACING AND BIPHASIC DEFIBRILLATION

FIELD OF THE INVENTION

This invention relates generally to apparatus for generating stimulation waveforms, and more particularly to a circuit for generating both pacing and defibrillation waveforms in an external unit.

BACKGROUND

One of the most common and life-threatening medical conditions is ventricular fibrillation, a condition where the human heart is unable to pump the volume of blood required by the human body. The generally accepted technique for restoring a normal rhythm to a heart experiencing ventricular fibrillation is to apply a strong electric pulse to the heart using an external cardiac defibrillator. External cardiac defibrillators have been successfully used for many years in hospitals by doctors and nurses, and in the field by emergency treatment personnel, e.g., paramedics.

Conventional external cardiac defibrillators first accumulate a high-energy electric charge on an energy storage capacitor. When a switching mechanism is closed, the stored energy is transferred to a patient in the form of a large current pulse. The current pulse is applied to the patient via a pair of electrodes positioned on the patient's chest. The switching mechanism used in most contemporary external defibrillators is a high-energy transfer relay. A discharge control signal causes the relay to complete an electrical circuit between the storage capacitor and a wave shaping circuit whose output is connected to the electrodes attached to the patient.

The relay used in contemporary external defibrillators has traditionally allowed a monophasic waveform to be applied to the patient. It has recently been discovered, however, that there may be certain advantages to applying a biphasic rather than a monophasic waveform to the patient. For example, preliminary research indicates that biphasic waveform may limit the resulting heart trauma associated with the defibrillation pulse.

The American Heart Association has recommended a range of energy levels for the first three defibrillation pulses applied by an external defibrillator. The recommended energy levels are: 200 joules for a first defibrillation pulse; 200 or 300 joules for a second defibrillation pulse; and 360 joules for a third defibrillation pulse, all within a recommended variance range of no more than plus or minus 15 percent according to standards promulgated by the Association for the Advancement of Medical Instrumentation (AAMI). These high energy defibrillation pulses are required to ensure that a sufficient amount of the defibrillation pulse energy reaches the heart of the patient and is not dissipated in the chest wall of the patient.

On the other hand, pacers are typically used to administer a series of relatively small electrical pulses to a patient experiencing an irregular heart rhythm. For example, each pacing pulse typically has an energy of about 0.05 J to 1.2 J. Because of the small energies used for pacing pulses, the circuitry used to generate the pacing pulses cannot typically be used for generating defibrillation pulses.

There are some systems that combine both a pacer and a defibrillator in a single unit for providing pacing pulses and defibrillation pulses as required. These conventional systems typically use separate defibrillation and pacing generation circuits. For example, FIG. 1 shows a combined pacing defibrillation unit 5 having a defibrillation circuit 6 and a pacing circuit 7. Unit 5 selectively delivers defibrillation or pacing pulses to the patient. Implantable systems generally use separate electrodes for pacing and defibrillation. An example of an implantable combined defibrillator/pacer is found in U.S. Pat. No. 5,048,521. Of course, having separate defibrillation and pacing circuits tends to increase the cost and size of the unit. In addition, because implantable defibrillators and pacers typically apply relatively low energy pulses, the output circuitry for such implantable units is generally not adaptable for use in an external unit.

The present invention is directed to an apparatus that overcomes the foregoing and other disadvantages in an external pacing/defibrillation unit. More specifically, the present invention is directed to a single output circuit for an external pacer/defibrillator that is capable of applying both high-energy biphasic defibrillation pulses and low-energy pacing pulses to a patient.

SUMMARY

In accordance with the present invention, an external defibrillator/pacer having an output circuit that is used in generating both a defibrillation pulse and a pacing pulse is provided. The output circuit includes four legs arrayed in the form of an "H" (hereinafter the "H-bridge output circuit"). Each leg of the output circuit contains a solid-state switch. By selectively switching on pairs of switches in the H-bridge output circuit, biphasic or monophasic defibrillation and pacing pulses may be applied to a patient.

In accordance with one aspect of the invention, the switches in three of the legs of the H-bridge output circuit are silicon controlled rectifiers (SCRs). A single SCR is used in each of these three legs. The switch in the fourth leg is an insulated gate bipolar transistor (IGBT). The bypass circuit is capable of conducting the relatively small pacing currents, which are generally too small to trigger the SCRs required to conduct the relatively large defibrillation currents. The addition of the bypass circuit eliminates the need for separate defibrillation and pacing output circuits.

In accordance with another aspect of the invention, the H-bridge output circuit has two IGBT legs and two SCR legs. The second IGBT leg allows the polarity of the defibrillation and pacing pulses to be opposite. In one embodiment, the pacing current is adjusted by adjusting the voltage on an energy storage capacitor.

In accordance with yet another aspect of the invention, instead of a bypass circuit, an adjustable current source is used to provide the pacing current. This current source is coupled to the energy storage capacitor. In one embodiment, the current source is an IGBT operated in the linear region.

In accordance with still another aspect of the invention, all of the H-bridge legs are implemented with IGBTs. This aspect allows for generation of biphasic pacing pulses. Further, by biasing the IGBTs in the linear region, the IGBTs can be used as current sources to control the pacing current. This would eliminate the need for a bypass circuit or separate current source.

BRIEF DESCRIPTION OF THE DRAWINGS

The foregoing aspects and many of the attendant advantages of this invention will become more readily appreciated by reference to the following detailed description, when taken in conjunction with the accompanying drawings listed below.

DETAILED DESCRIPTION

Figure 1:
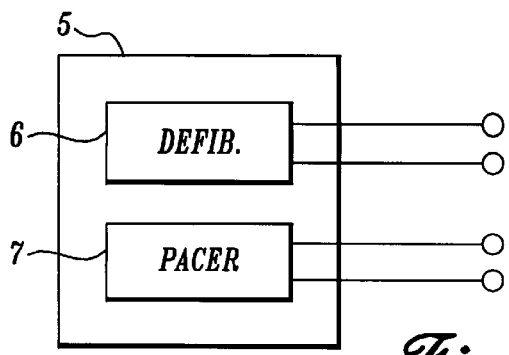
FIG. 1 is a block diagram of a conventional combined defibrillator/pacer unit.
Figure 2:
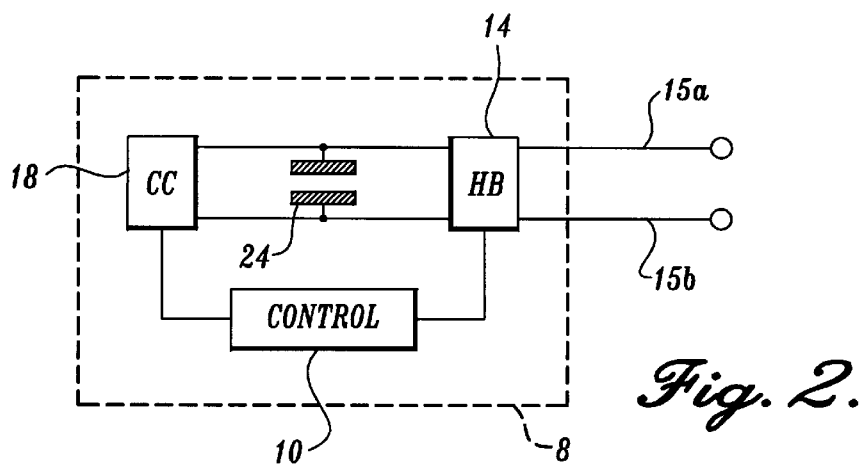
FIG. 2 is a block diagram illustrative of a combined defibrillator/pacer unit having a single output circuit, according to one embodiment of the present invention.

FIG. 2 is a block diagram illustrative of an external combined defibrillator/pacer 8, according to one embodiment of the present invention. Combined external defibrillator/pacer 8 includes a control circuit 10, an H-bridge 14, electrodes 15a and 15b, a charging circuit 18, and an energy storage capacitor 24.

Defibrillator/pacer 8 is interconnected as follows. Control circuit 10 is connected to charging circuit 18 and H-bridge 14. Charging circuit 18 is connected to energy storage capacitor 24. H-bridge 14 is connected to the electrodes of energy storage capacitor 24, and also to electrodes 15a and 15b. Electrodes 15a and 15b are used to administer defibrillation and pacing pulses transcutaneously to a patient. The operation of defibrillator/pacer 8 is described below in conjunction with FIG. 3.

Figure 3:
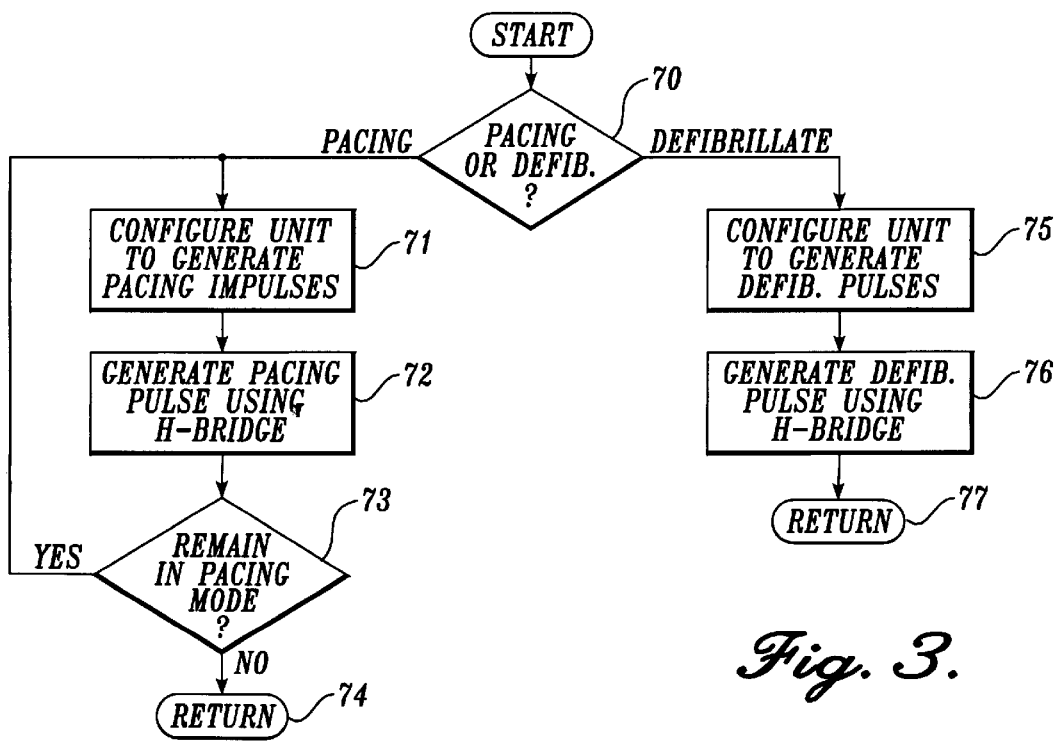
FIG. 3 is a flow diagram illustrative of the operation of the combined defibrillator/pacer unit depicted in FIG. 2.

FIG. 3 is a flow diagram illustrative of the operation of defibrillator/pacer 8. Referring to FIGS. 2 and 3, defibrillator/pacer 8 operates as follows. In a step 70, defibrillator/pacer 8 decides whether pacing or defibrillation pulses are appropriate for the patient. Alternatively, the user may make this determination. If pacing pulses are appropriate, in a next step 71, defibrillator/pacer 8 is configured to generate pacing pulses. For example, in this step, control circuit 10 can control charging circuit 18 to charge energy storage capacitor 24 to a desired level for pacing. Then in a next step 72, defibrillator/pacer 8 generates a pacing pulse using H-bridge 14. As described below, control circuit 10 may be configured to control H-bridge 14 to generate monophasic or biphasic pacing pulses of different polarities.

In a next step 73, it is determined whether defibrillator/pacer 8 should remain in the pacing mode. If defibrillator/pacer 8 is to remain in the pacing mode, the process returns to step 71. Otherwise, a step 74 is performed in which external combined defibrillator/pacer 8 returns to a standby mode.

On the other hand, if in step 70, it is determined that a defibrillation pulse is appropriate, in a step 75, defibrillator/pacer 8 is configured to generate a defibrillation pulse. In a next step 76, defibrillator/pacer 8 generates a defibrillation pulse using H-bridge 14. The generation of a defibrillation pulse is described further below in conjunction with FIG. 4. Then in a next step 77, the process returns to the standby mode.

Figure 4:
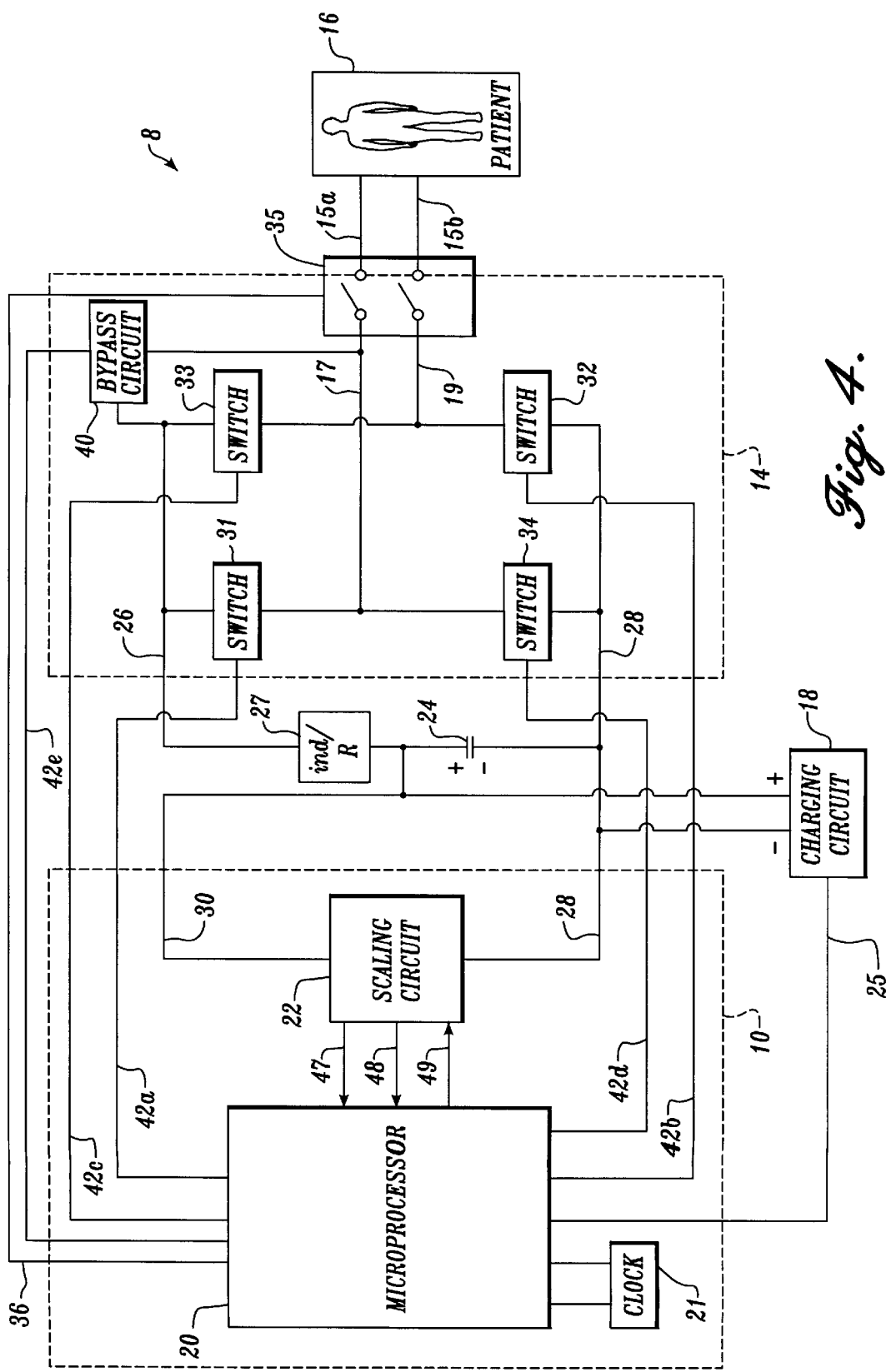
FIG. 4 is a more detailed block diagram illustrative of the combined defibrillator/pacer unit depicted in FIG. 2.

FIG. 4 is a more detailed block diagram of external combined defibrillator/pacer 8 that is connected to a patient 16. The defibrillator includes a microprocessor 20 that is connected to energy storage capacitor 24 via charging circuit 18. It will be appreciated by those skilled in the art that energy storage capacitor 24 may be implemented with a multi-capacitor network (i.e., with capacitors connected in series and/or parallel). During the operation of the defibrillator, microprocessor 20 controls charging circuit 18 using a signal on a control line 25 to charge energy storage capacitor 24 to a desired voltage level. To monitor the charging process, microprocessor 20 is connected to a scaling circuit 22 by a pair of measurement lines 47 and 48, and by a control line 49. Scaling circuit 22 is connected to energy storage capacitor 24 by a bridge line 28, which connects to the negative lead of energy storage capacitor 24, and by a line 30, which connects to the positive lead of the capacitor. A clock 21 is also connected to microprocessor 20.

Scaling circuit 22 is used to step down the voltage across energy storage capacitor 24 to a range that may be monitored by microprocessor 20. Scaling circuit 22 is described briefly below and in more detail in an application entitled "Method and Apparatus for Verifying the Integrity of an Output Circuit Before and During Application of a Defibrillation Pulse", U.S. patent application Ser. No. 08/811,834, filed Mar. 5, 1997, and incorporated herein by reference. Energy storage capacitor 24 can be charged to a range of voltage levels, with the selected level depending on the patient and other parameters. Preferably, the size of energy storage capacitor 24 falls within a range from 150 $\mu$F to 200 $\mu$F. In order to generate the necessary defibrillation pulse for external application to a patient, energy storage capacitor 24 is charged to between 100 volts and 2,200 volts. To detect small percentage changes in the selected voltage level of energy storage capacitor 24, scaling circuit 22 is adjustable to measure different voltage ranges. The adjusted output is measured by microprocessor 20 on measurement line 48.

After charging to a desired level, the energy stored in energy storage capacitor 24 may be delivered to patient 16 in the form of a defibrillation pulse. H-bridge 14 is provided to allow the controlled transfer of energy from energy storage capacitor 24 to patient 16. H-bridge 14 is an output circuit that includes four switches 31, 32, 33, and 34. Each switch is connected in a leg of the output circuit that is arrayed in the form of an "H". Switches 31 and 33 are coupled through a protective component 27 to the positive lead of the energy storage capacitor 24 by a bridge line 26. Protective component 27 limits the current and voltage changes from energy storage capacitor 24, and has both inductive and resistive properties. Switches 32 and 34 are coupled to energy storage capacitor 24 by a bridge line 28. Patient 16 is connected to the left side of H-bridge 14 by an apex line 17, and to the right side of H-bridge 14 by a sternum line 19. As depicted in FIG. 4, apex line 17 and sternum line 19 are connected to electrodes 15a and 15b, respectively, by a patient isolation relay 35. Microprocessor 20 is connected to switches 31, 32, 33, and 34 by control lines 42a, 42b, 42c, and 42d, respectively, and to patient isolation relay 35 by control line 36. A bypass circuit 40 is connected between bridge line 26 and apex line 17. Bypass circuit 40 is also connected to receive a control signal from microprocessor 20 through control line 42e. Bypass circuit 40 is implemented with a switch to bypass switch 33 when generating pacing pulses, as described below.

Application of appropriate control signals by microprocessor 20 over the control lines causes switches 31–34 to be appropriately opened and closed and bypass circuit 40 to be opened, thereby allowing H-bridge 14 to conduct energy from energy storage capacitor 24 to patient 16 in the form of a defibrillation pulse.

In a similar manner, microprocessor 20, through appropriate application of the control signals, causes switches 31-34 to be appropriately opened and closed and bypass circuit 40 to be closed, thereby allowing H-bridge 14 to conduct energy from storage capacitor 24 to the patient in the form of a monophasic pacing pulse. Bypass circuit 40 is needed to bypass switch SW33 because an SCR is used to implement this switch. More specifically, at the size required to handle the defibrillation energies, the SCR generally cannot be triggered by a typical pacing pulse current.

Figure 5:
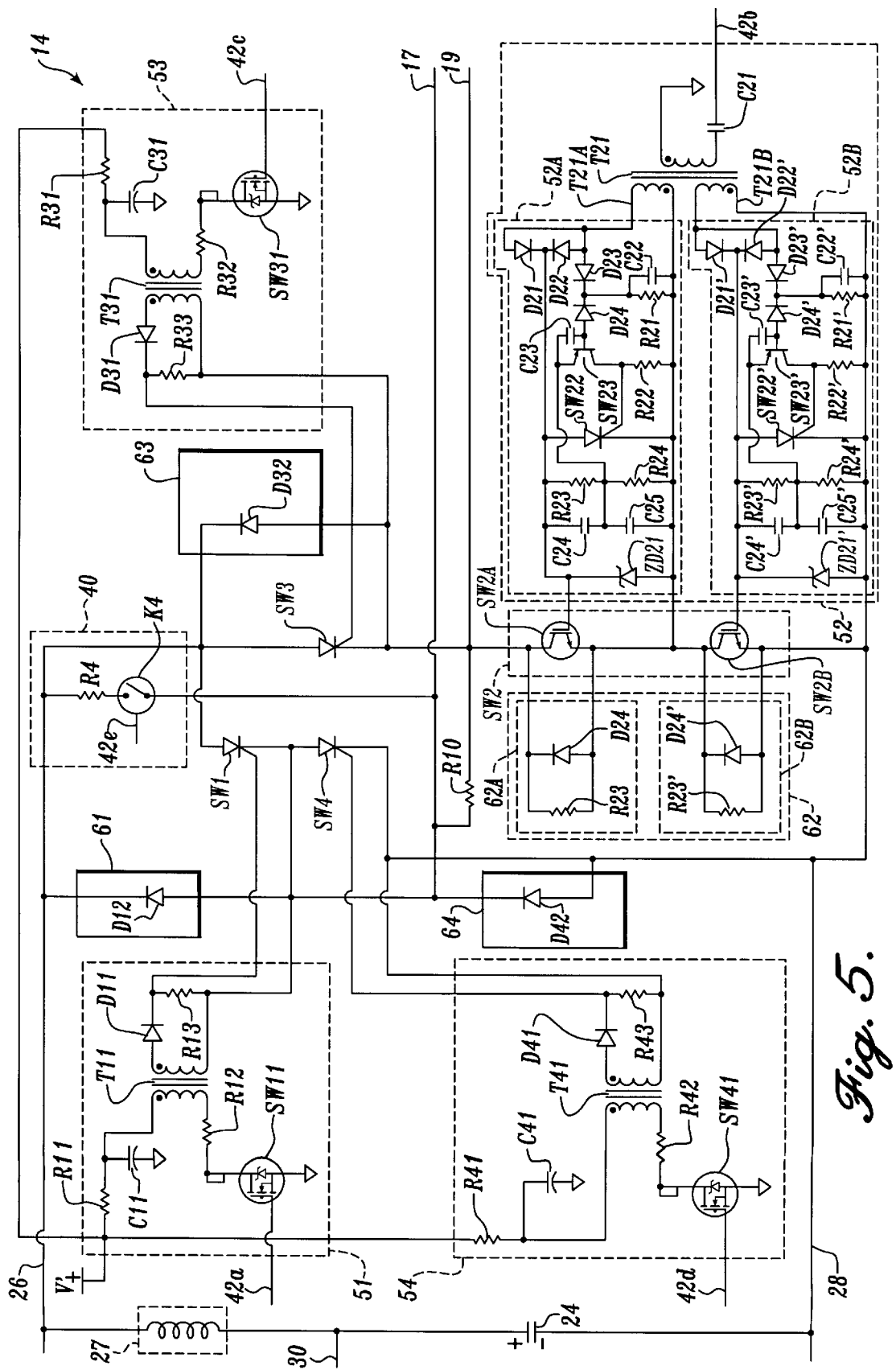
FIG. 5 is a schematic diagram illustrative of the block diagram depicted in FIG. 4.

A preferred construction of H-bridge 14 is shown in FIG. 5. H-bridge 14 uses four output switches SW1–SW4 to conduct energy from energy storage capacitor 24 to patient 16. Switches SWl, SW3 and SW4 are semiconductor switches, preferably silicon controlled rectifiers (SCRs). Switch SW2 is a series combination of switches SW2A and SW2B, preferably both insulated gate bipolar transistors (IGBTs). In this embodiment, the IGBTs are model IXHS1718 IGBTs available from IXYS, Santa Clara, Calif. Two model IXHS1718 IGBTs are used in "series" to withstand the maximum voltage that may occur across switch SW2 in H-bridge 14 so that the voltage across the entire switch SW2 is divided between the two IGBTs.

Alternatively, a single IGBT having a sufficient voltage rating may be used in the output circuit, where such an IGBT is available. Switches SW1–SW4 can be switched from an off(non-conducting) to an on (conducting) condition.

In the defibrillation mode, defibrillator/pacer 8 generates a biphasic defibrillation pulse for application to the patient 16. Initially, switches SW1–SW4 are opened. Charging of energy storage capacitor 24 is started, and monitored by microprocessor 20 (FIG. 4). When energy storage capacitor 24 is charged to a selected energy level and patient isolation relay 35 is closed, switches SW1 and SW2 are switched on so as to connect energy storage capacitor 24 with apex line 17 and sternum line 19 for the application of a first phase of a defibrillation pulse to patient 16. The stored energy travels from the positive terminal of energy storage capacitor 24 on line 26, through switch SW1 and apex line 17, across patient 16, and back through sternum line 19 and switch SW2 to the negative terminal of energy storage capacitor 24 on line 28. The first phase of the biphasic pulse is therefore a positive pulse from the apex to the sternum of patient 16.

Before energy storage capacitor 24 is completely discharged, switch SW2 is biased off to prepare for the application of the second phase of the biphasic pulse.

Once switch SW2 is biased off, switch SW1 will also become non-conducting because the voltage across the SCR falls to zero.

After the end of the first phase of the biphasic defibrillation pulse, switches SW3 and SW4 are switched on to start the second phase of the biphasic pulse. Switches SW3 and SW4 provide a current path to apply a negative defibrillation pulse to patient 16. The energy travels from the positive terminal of energy storage capacitor 24 on line 26, through switch SW3 and sternum line 19, across patient 16, and back through apex line 17 and switch SW4 to the negative terminal of energy storage capacitor 24 on line 28. The polarity of the second phase of the defibrillation pulse is therefore opposite in polarity to the first phase of the biphasic pulse. The end of the second phase of the biphasic pulse is truncated by switching on switch SW1 to provide a shorted path for the remainder of the capacitor energy through switches SW1 and SW4. After energy storage capacitor 24 is discharged, switches SW1–SW4 are switched off. Patient isolation relay 35 is then opened. Energy storage capacitor 24 may then be recharged to prepare defibrillator/pacer 8 to apply another defibrillation pulse or to apply pacing pulses.

As described above, the four output switches SW1–SW4 can be switched from an off (nonconducting) state to an on (conducting) state by application of appropriate control signals on control lines 42a, 42b, 42c, and 42d. In order to allow the SCRs and IGBTs to switch the high voltages in an external defibrillator, special switch driving circuits 51, 52, 53 and 54 are coupled to switches SW1–SW4, respectively.

Control lines 42a, 42b, 42c, and 42d are connected to switch driving circuits 51, 52, 53, and 54, to allow microprocessor 20 to control the state of the switches.

Switch driving circuits 51, 53 and 54 are identical. For purposes of this description, therefore, only the construction and operation of switch driving circuit 51 will be described. Those skilled in the art will recognize that switch driving circuits 53 and 54 operate in a similar manner.

Switch driving circuit 51 includes a control switch SW11, resistors R11, R12, and R13, a capacitor C11, a diode D11 and a high-voltage transformer T11.

Resistor R11 is connected between the positive voltage supply V'+ and the dotted end of the primary winding of transformer T11, and capacitor C11 is connected between ground and the dotted end of the primary winding of transformer T11. Resistor R12 is connected between the non-dotted end of the primary winding of transformer T11 and the drain of control switch SW11. Resistors R11 and R12 and capacitor C11 limit and shape the current and voltage waveforms across the primary winding of transformer T11. The source of control switch SW11 is connected to ground, and the gate of control switch SW11 is connected to control line 42a.

On the secondary winding side of transformer T11, the anode of diode D1 is connected to the dotted end of the secondary winding of transformer T11, and the cathode of diode D11 is connected to the gate of SCR switch SW1. Resistor R13 is connected between the cathode of diode D11 and the non-dotted end of the secondary winding of transformer T11. The non-dotted end of the secondary winding of transformer T11 is connected to the cathode of SCR switch SW1.

To turn on switch SW1, an oscillating control signal is provided on control line 42a. In this embodiment, the oscillating control signal is a pulse train. The pulse train control signal repeatedly turns control switch SW11 on and off, producing a changing voltage across the primary winding of transformer T11. The voltage is stepped down by transformer T11 and rectified by diode D11 before being applied to the gate of SCR switch SW1. In a preferred embodiment, a 10% duty cycle pulse train on the control line 42a has been found to be adequate to maintain SCR switch SW1 in a conducting state. As long as the control signal is applied to the switch driving circuit 51, the switch SW1 will remain in the conducting state. The switch SW1 remains in the conducting state even when conducting relatively low defibrillation currents. In one embodiment, the SCR switches can conduct currents as low as 90 mA. As is well known, once triggered or latched on, an SCR generally remains in the conducting state until the current through the SCR drops below a minimum level, even if the gate voltage of the SCR is grounded. Thus, when the current through the SCR switch would not be 90 mA or greater, the SCR would not conduct. Thus, SCRs are generally not practical for pacing applications.

A different switch driving circuit is required to turn on the IGBT switches of switch SW2. Switch driving circuit 52 includes a capacitor C21, a transformer T21, and two identical switch driving circuits 52A and 52B, each circuit corresponding to one of the IGBTs. On the primary winding side of transformer T21, capacitor C21 is connected between control line 42b and the non-dotted end of the primary winding of transformer T21. The dotted end of the primary winding of transformer T21 is grounded.

Transformer T21 has two secondary windings T21A and T21B, one for each of switch driving circuits 52A and 52B. Switch driving circuits 52A and 52B are identical, and therefore only the construction and operation of switch driving circuit 52A will be described. Switch driving circuit 52A includes diodes D21, D22, 23, and D24, Zener diode ZD21, capacitors C22, C23, C24, and C25, resistors R21, 22, R23, and R24, a PNP switch SW23, and an SCR switch SW22.

The anodes of diodes D21, D22, and D23 are connected to the non-dotted end of secondary winding T21A of transformer T21. The cathodes of diodes D21 and D22 are connected to the gate of IGBT switch SW2A. Resistor R21 and capacitor C22 are connected between the dotted end of secondary winding T21A of transformer T21 and the cathode of diode D23. The anode of SCR switch SW22 and the cathode of Zener diode ZD21 are connected to the gate of IGBT switch SW2A. The cathode of SCR switch SW22 and the anode of Zener diode ZD21 are connected to the dotted end of secondary winding T2IA of transformer T21, and also to the emitter of IGBT switch SW2A.

Resistor R23 and capacitor C24 are connected between the gate of IGBT switch SW2A and the emitter of PNP switch SW23. Resistor R24 and capacitor C25 are connected between the emitter of PNP switch SW23 and the dotted end of secondary winding T21A of transformer T21. The gate of SCR switch SW22 is connected to the collector of PNP switch SW23. Resistor R22 is connected between the collector of PNP switch SW23 and the dotted end of secondary winding T21 A of transformer T21. Capacitor C23 is connected between the emitter and the base of PNP switch SW23. The anode of diode D24 is connected to the base of PNP switch SW23, and the cathode of diode D24 is connected to the cathode of diode D23.

To turn on IGBT switch SW2A, an oscillating control signal is provided on control line 42b. In this embodiment, the oscillating control signal is a pulse train. The pulse train control signal is stepped up in voltage by transformer T21 and applied to the input of switch driving circuit 52A. During a positive pulse of the control signal on control line 42b, diodes D21 and D22 rectify the current that travels through secondary winding T21A to charge capacitors C24 and C25. As will be discussed in more detail below, some current also travels through diode D23 to charge capacitor C22.

Capacitor C21 limits the current in the primary winding of transformer T21, which correspondingly limits the current in secondary winding T21A. The secondary winding current determines the charging time of the capacitors C24 and C25. Since the voltage across capacitors C24 and C25 is also the voltage on the gate of IGBT switch SW2A, a slow accumulation of voltage on capacitors C24 and C25 therefore results in a slow turn on of IGBT switch SW2A. The charging current is selected so that IGBT switch SW2A is turned on relatively slowly when compared to the fast turn on of SCR switches SWI, SW3, and SW4. A slow turn-on for IGBT switch SW2A is desirable because the IGBT switches are on the same side of H-bridge 14 as SCR switch SW3. SCR switch SW3 is controlled by the control signal on control line 42c, but due to the nature of SCR switches, the SCR switch may be accidentally turned on regardless of the signal on control line 42c if a rapid voltage change occurs across SCR switch SW3. If IGBT switches SW2A and SW2B were therefore turned on too quickly, the resulting rate of change of the voltage across SCR switch SW3 might cause it to turn on accidentally.

Zener diode ZD21 protects IGBT switch SW2A by regulating the maximum voltage across capacitors C24 and C25. Without Zener diode ZD21, the voltage on the gate of IGBT switch SW2A would rise to a level that would damage IGBT switch SW2A.

Also during the positive pulse of the pulse train control signal on control line 42b, diode D23 rectifies the current that travels through secondary winding T21A to charge capacitor C22. The charge on capacitor C22, which is replenished on each positive pulse of the pulse train control signal, maintains the voltage across the base of PNP switch SW23 above the turn-on level for the PNP switch. PNP switch SW23 turns on if the base voltage on the switch drops below a threshold level. As will be described below, PNP switch SW23 is only turned on when IGBT switch SW2A is to be turned off. Capacitor C23 and diode D24 are also provided to prevent PNP switch SW23 from turning on. Capacitor C23 serves as a high frequency filter to prevent the high frequency driving pulses of switch driving circuit 52A from causing PNP switch SW23 to spuriously turn on. Diode D24 prevents a large negative base-emitter voltage from occurring which could cause PNP switch SW23 to enter reverse breakdown.

Since some discharging of capacitor C22 occurs through resistor R21 between positive pulses of the control signal on control line 42b, resistor R21 must be large enough to limit the discharging current flow from capacitor C22 between the pulses. Limiting the current flow prevents the voltage on capacitor C22 from dropping below the threshold level sufficient to turn on PNP switch SW23 between pulses of the control signal. Then, during a positive pulse of the pulse train control signal on control line 42b, the charging of capacitor C22 must be sufficient to counteract the discharging that occurred since the previous positive pulse so as to return capacitor C22 to its fully charged level by the end of the positive pulse.

In the preferred embodiment, a 2 MHz pulse train control signal with a 25% duty cycle on the control line 42b has been found to be adequate to maintain the conducting state of IGBT switches SW2A and SW2B. The switches will remain conducting as long as the control signal is present, and regardless of the current flowing through the switches. Conversely, when the control signal is not present, IGBT switches SW2A and SW2B will be non-conductive.

The maximum current that may generally occur in H-bridge 14 results from the undesirable situation where a user of defibrillator/pacer 8 places the two shock paddles directly in contact with one another. When this happens, a short circuit is created between apex line 17 and sternum line 19. During a short circuit, a brief current of up to 400 amps can result. In this embodiment, to accommodate the short circuit current without damaging IGBT switches SW2A and SW2B, IGBT switches SW2A and SW2B are biased by a thirty volt gate voltage. Biasing the IGBTs at this voltage level is successful since the IGBT switches are used in a pulsed manner. If IGBT switches SW2A and SW2B were driven continuously for long periods of time with thirty volts on their gates, they might be damaged, but in H-bridge 14, they are only driven at this level for very brief intervals.

In contrast to the slow turn-on of IGBT switches SW2A and SW2B, the turnoff of the IGBT switches is performed relatively quickly. The IGBT switches may be quickly turned off because at turn-off there is no concern that the sensitive SCR switches will accidentally turn on. In addition, a fast turn-off is desirable to reduce the time that an IGBT switch would be subjected to a high voltage if one of the IGBT switches is inadvertently turned off before the other.

IGBT switches SW2A and SW2B are turned off when the pulse train control signal on control line 42b is removed. Once positive voltage pulses are no longer being induced in the secondary windings of transformer T21, driving circuits 52A and 52B begin the turn-off process. Again, the turn-off process will only be described with respect to driving circuit 52A since the circuits are essentially identical.

During the turn-off process, capacitor C22 begins discharging through resistor R21. Since the RC time constant of capacitor C22 and resistor R21 is much smaller than the RC time constant of capacitors C24 and C25 and resistors R23 and R24, the discharging of capacitor C22 occurs much more quickly than the discharging of capacitors C24 and C25. When the voltage on capacitor C22 drops below a threshold voltage level, PNP switch SW23 is turned on. The threshold voltage level is equivalent to the base turn-on voltage of PNP switch SW23, plus the voltage drop across diode D24. Once PNP switch SW23 is turned on, discharge current from capacitor C25 begins to flow through the switch. As the current increases, the voltage across resistor R22 correspondingly increases. When the voltage across resistor R22 reaches a sufficient voltage level, SCR switch SW22 is turned on, providing a shorted path for the remainder of the energy stored in capacitors C24 and C25. The rapid discharge of capacitors C24 and C25 causes a corresponding rapid drop in the gate voltage of IGBT switch SW2A, quickly turning off the switch. Resistors R23 and R24 are provided across capacitors C24 and C25 to control the voltage division across the capacitors.

It will be appreciated that special driving circuits 52A and 52B allow the IGBTs to be used in external defibrillator/pacer 8 where extremely high voltages must be switched in the presence of SCRs. The driving circuits minimize the number of components required to switch a defibrillation pulse of 200 or more joules. In addition to conducting high currents associated with high-energy defibrillation pulses, the IGBTs are also able to conduct very low currents that are associated with defibrillation pulses of less than 50 joules.

As shown in FIG. 5, each switch SW1–SW4 is also connected in parallel with a switch protection circuit 61, 62, 63, and 64, respectively. The switch protection circuits are designed to prevent spurious voltage spikes from damaging the switches in H-bridge 14. Switch protection circuits 61, 63 and 64 are identical and therefore only the construction and operation of switch protection circuit 61 will be described.

Switch protection circuit 61 includes a diode D12. The cathode of diode D12 is connected to the anode of SCR switch SW1, and the anode of diode D12 is connected to the cathode of SCR switch SW1. Diode D12 protects SCR switch SW1 against negative inductive spikes that may occur due to cable or load inductance.

Switch protection circuit 62 includes two identical switch protection circuits 62A and 62B, which protect IGBT switches SW2A and SW2B, respectively. Since switch protection circuits 62A and 62B are essentially identical, only the construction and operation of switch protection circuit 62A will be described. Switch protection circuit 62A includes a diode D24 and a resistor R23. Resistor R23 is connected between the collector and the emitter of IGBT switch SW2A. The cathode of diode D24 is connected to the collector of IGBT switch SW2A, and the anode of diode D24 is connected to the emitter of IGBT switch SW2A.

Diode D24 operates similarly to diode D12 as described above in that it protects IGBT switch SW2A against negative inductive spikes. Resistor R23 (in conjunction with resistor R23') ensures that the voltage across the two IGBT switches SW2A and SW2B is equally divided when H-bridge 14 is at rest. Dividing the voltage across IGBT switches SW2A and SW2B is important due to the limitations of present IGBT technology, which limits the rating of each IGBT switch to 1200V. In a system where the total maximum voltage is 2200V, the maximum voltage ratings are therefore obeyed by dividing the maximum voltage across each IGBT switch.

Additional protection to the switches is provided by protective component 27, which has both inductive and resistive properties. In one embodiment, protective circuit 27 is implemented with coil of resistance wire that provides an inductive resistance. Protective component 27 limits the rate of change of the voltage across, and current flow to, SCR switches SW1, SW3, and SW4. Too high of a rate of change of the voltage across an SCR switch is undesirable because it can cause the SCR switch to inadvertently turn on. For example, since SCR switches SW1 and SW4 are on the same side of H-bridge 14, any time SCR switch SW4 is abruptly turned on, a rapid voltage change may also result across SCR switch SW1. To prevent rapid voltage changes, protective component 27 reduces the rate of change of the voltage across SCR switch SW1 when SCR switch SW4 is turned on. Also, too high of a current flow can damage the switches SWl, SW3 and SW4, and protective component 27 limits the current flow in H-bridge 14. The use of protective component 27 therefore reduces the need for additional protective components that would otherwise need to be coupled to switches SW1, SW3 and SW4.

It will be appreciated that a great advantage of H-bridge 14 described above is that it allows external defibrillator/pacer 8 to generate and apply a high-energy biphasic waveform to a patient. For prior defibrillators providing a monophasic waveform, the standard energy level in the industry for the discharge has been greater than 200 joules. The above described circuit allows the same amount of energy (more than 200 joules) to be delivered to the patient in a biphasic waveform, thereby resulting in a greater certainty of defibrillation effectiveness for a broader range of patients. At the same time, the circuit incorporates special driving circuitry to allow even very low energy biphasic waveforms (less than fifty joules) to be delivered to the patient.

The above described defibrillation mode operation is similar to the operation of the external defibrillator circuit disclosed in co-pending and commonly assigned U.S. patent application Ser. No. 08/811,833 filed Mar. 5, 1997, entitled "H-Bridge Circuit For Generating A High-Energy Biphasic Waveform In An External Defibrillator" by J. L. Sullivan et al. In a manner similar to the defibrillator disclosed in the Ser. No. 08/811,833 application, this embodiment of defibrillator/pacer 8 generates a biphasic defibrillation pulse with a positive first phase and a negative second phase (measured from apex line 17 to sternum line 19).

Figure 6:
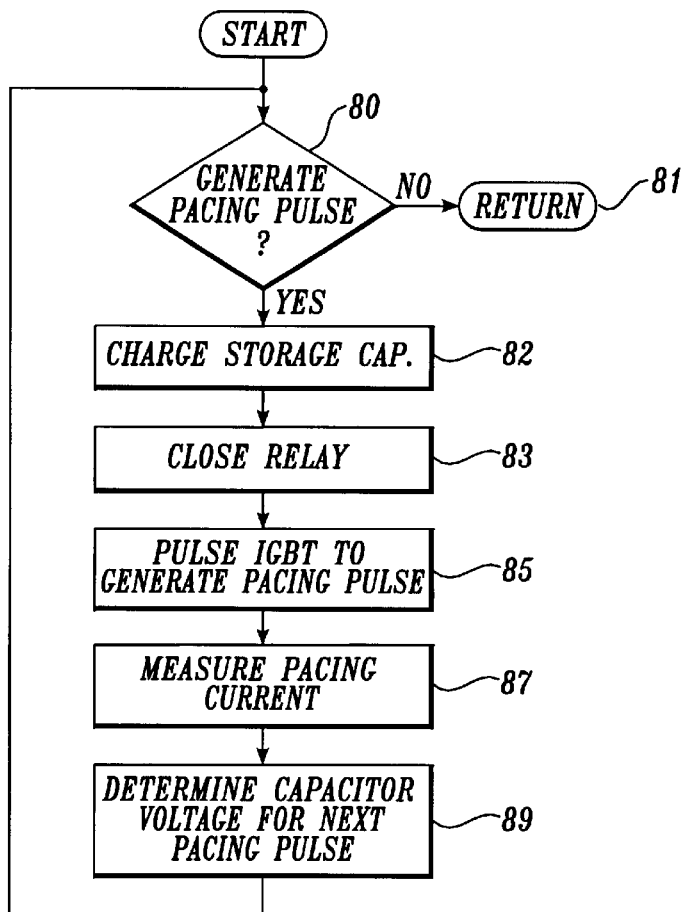
FIG. 6 is a flow diagram illustrative of the operation of the combined defibrillator/pacer unit depicted in FIG. 5.

The operation of this embodiment of defibrillator/pacer 8 in the pacing mode is represented by the flow diagram of FIG. 6. In view of the present disclosure, those skilled in the art can implement, without undue experimentation, a suitable software or firmware program to be executed by microprocessor 20 of control circuit 10 to perform functions represented in FIG. 6. Referring to FIGS. 4, 5, and 6, defibrillator/pacer 8 operates as follows. Initially, switches SW1–SW4 and bypass circuit 40 are opened. Once configured in the pacing mode, in a step 80, control circuit 10 determines whether to generate a pacing pulse. If no pacing pulse is to be generated, the process returns to the standby mode in a step 81. However, if a pacing pulse is to be generated, in a next step 82, control circuit 10 causes charging circuit 18 to charge energy storage capacitor 24 to a capacitor voltage level of about twenty-five to three hundred volts. The capacitor voltage level would vary according to desired pacing current for the pending pacing pulse, as described below.

In a next step 83, control circuit 10 causes a relay K4 in bypass circuit 40 to close. In one embodiment, relay K4 is implemented with two model RTD19005 relays available from Potter-Bromfield, Princeton, Ind. When relay K4 is closed, a conductive path is formed between the positive electrode of energy storage capacitor 24, through line 28, through a resistor R4, through relay K4 and to apex line 19 As a result, switch SW3 is bypassed. Resistor R4 has a value of about five hundred ohms to help limit the short circuit current if the paddles touch.

In a next step 85, control circuit 10 pulses on IGBTs SW2A and SW2B to allow a monophasic pacing pulse to be applied to patient 16. In this embodiment, control circuit 10 controls the duration that IGBTs SW2A and SW2B are pulsed on to be equal to the desired duration of the monophasic pacing pulse. For a given capacitance value of energy storage capacitor 24, the droop of the pacing pulses would vary according to patient impedance.

In a step 87, control circuit 10 measures the pacing current as the pacing pulse is being applied to patient 16. In one embodiment, the pacing current is measured by monitoring the voltage drop across resistor R4. Alternatively, the pacing current can be measured by monitoring the change in voltage of energy storage capacitor 24. In a next step 89, control circuit 20 determines the capacitor voltage level across energy storage capacitor 24 that is required for the next pacing pulse. In this embodiment, the current of the next pacing pulse is increased by about 5 mA. That is, during pacing, the pacing current is increased in 5 mA increments until the pacing pulses are of sufficient strength to cause the heart muscle to contract or to a maximum of about 200 mA. The process then returns to step 80 to generate the next pacing pulse.

Figure 7:
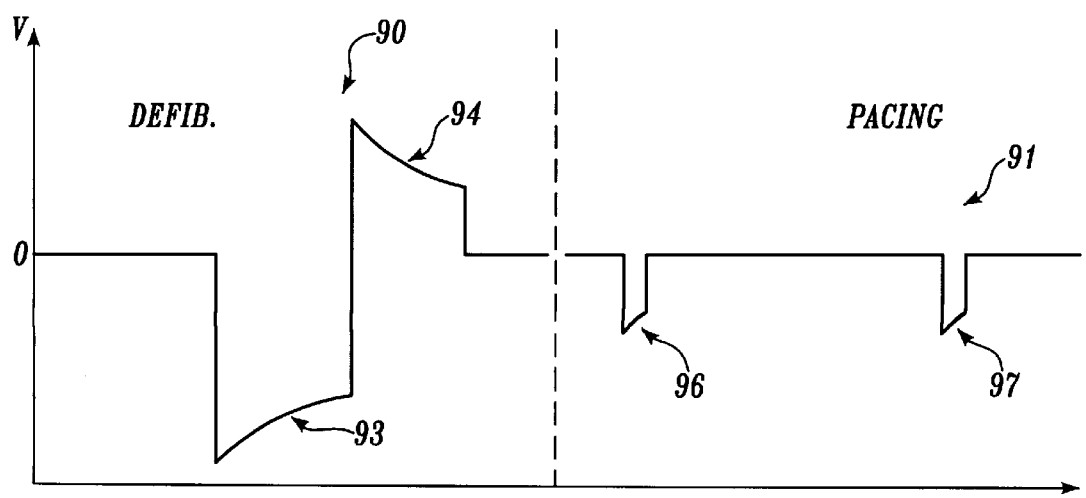
FIG. 7 is a diagram illustrative of the waveforms generated by the combined defibrillator/pacer unit depicted in FIG. 5, according to one embodiment of the present invention.

The pacing pulses generated by this embodiment are positive (measured from apex line 17 to sternum line 19). However, because the polarity of a pacing pulse affects pacing capture threshold, the general practice is to generate pacing pulses that are negative. Negative pacing pulses can be generated by simply by switching apex and sternum lines 17 and 19. FIG. 7 shows waveforms representing the waveforms generated by this alternative embodiment. Waveform 90 represents a biphasic defibrillation pulse generated by this alternative, while waveform 91 represents a monophasic pacing pulse sequence. Due to the switching of apex and sternum lines 17 and 19 in this embodiment, defibrillation waveform 90 has a negative first phase 93 and a positive second phase 94. Pacing waveform 91 has negative monophasic pulses 96, 97 and so on. Although not shown in FIG. 7, the biphasic waveforms may have a small delay portion of about zero volts between the first and second phases.

Although this alternative embodiment generates negative pacing pulses, the polarity of the defibrillation pulse phases is reversed. Current research tends to show that the polarity of monophasic defibrillation pulses is not significant. This finding may also apply to biphasic defibrillation pulses. Accordingly, this embodiment may be practical for use in the field.

Figure 8:
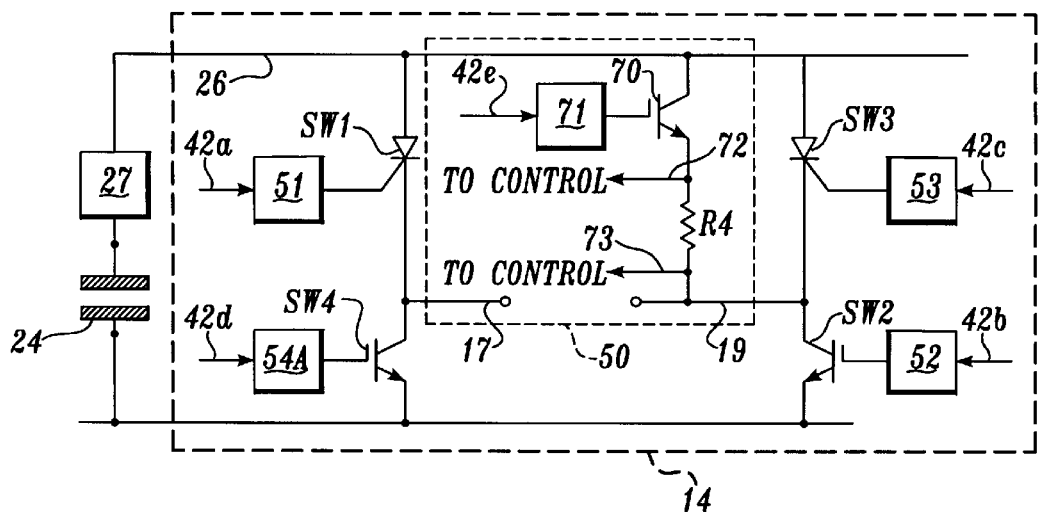
FIG. 8 is a block diagram illustrative of another embodiment of a combined defibrillator/pacer unit, according to the present invention.

FIG. 8 is a block diagram of an alternative embodiment of H-bridge 14 that is advantageously used to generate defibrillation and pacing pulses with opposite polarity. This embodiment is similar to the embodiment of FIG. 5 except that the embodiment of FIG. 8 uses an IGBT to implement switch SW4. Thus, switches SW1, SW2 and SW3 and driving circuits 51, 52 and 53 of FIG. 8 are implemented as in the embodiment of FIG. 5. Because switch SW4 is an IGBT switch, switch driving circuit 54A is essentially identical to switch driving circuit 52 used for driving IGBT switch SW2. In addition, the embodiment of FIG. 8 uses a switch driving circuit 54A and a current source circuit 50 instead of the switch driving circuit 54 and bypass circuit 40 of FIG. 5.

In one embodiment, current source circuit 50 is implemented with an IGBT circuit 70. An IGBT circuit is used because the circuit must be strong enough to withstand the relatively large voltages used in the defibrillation mode. IGBT circuit 70 is connected to line 26 and resistor R4. In this embodiment, resistor R4 has a value of about IOQ. Resistor R4 is also connected to sternum line 19. When conductive, IGBT circuit 70 provides a current path from line 26 to resistor R4 and on to sternum line 19. A switch driving circuit 71 is connected to control line 42e and the gate of IGBT circuit 70. Switch driving circuit 71 turns IGBT circuit 70 off and on in response to a control signal from control circuit 10 received on control line 42e.

In addition, in this embodiment, control circuit 10 (FIG. 4) is connected to monitor the voltage across resistor R4 via lines 72 and 73 during the pacing mode. Control circuit 10 (FIG. 4) is configured to provide the control signal over control line 42e to cause switch driving circuit 71 to operate IGBT circuit 70 in the linear region so that the current conducted by IGBT circuit 70 can be adjusted to a desired level. This technique is referred to herein as constant current pacing because the current can be maintained at a constant peak level even if patient impedance changes between pulses and is not adjusted with regard to the energy discharged by energy storage capacitor 24. Switch driving circuit 71 is described further below in conjunction with FIG. 10.

Figure 9:
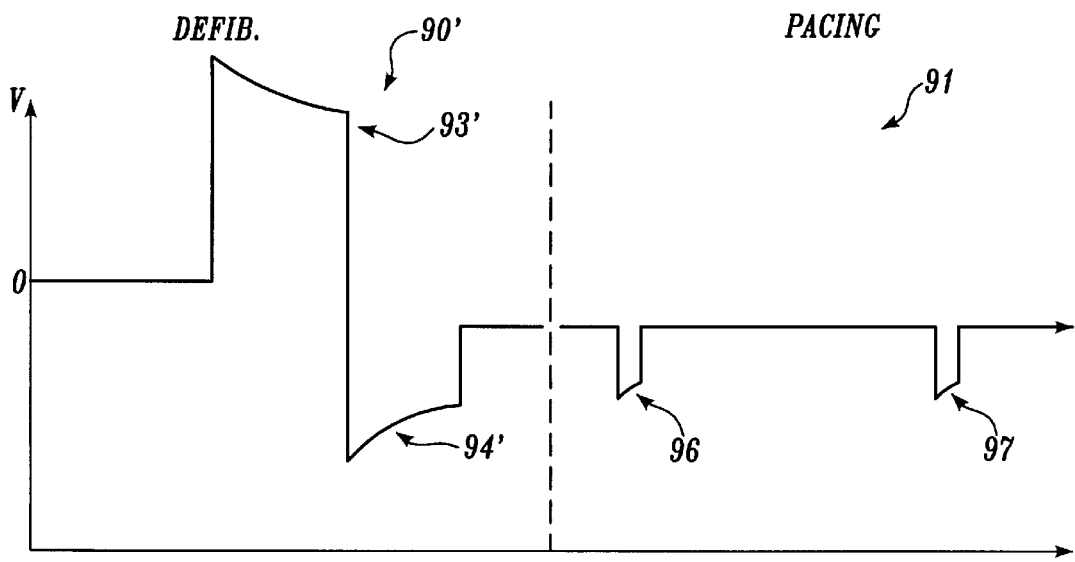
FIG. 9 is a diagram illustrative of the waveforms generated by the combined defibrillator/pacer unit depicted in FIG. 8, according to one embodiment of the present invention.

In the defibrillation mode, current source circuit 50 is turned off and switches SW1 and SW2 are turned on to generate the first phase of the biphasic defibrillation pulse. As shown in FIG. 9, this switching sequence generates biphasic defibrillation waveform 90' with a first phase 93' that is positive. To generate the second phase, switch SW2 is turned off. As described above for the embodiment of FIG. 5, turning off switch SW2 causes switch SW1 to turn off. Then switches SW3 and SW4 are turned on. As a result, second phase 93' in FIG. 9 is negative. Switches SW1, SW2 and SW3 are turned off and off in essentially the same manner as described above for the embodiment of FIG. 5. Switch SW4 is turned off and on in essentially the same manner as switch SW2.

In the pacing mode, current source circuit 50 and switch SW4 are turned on. Current source circuit 50 is controlled by control circuit 10 (FIG. 4) to provide a desired level of pacing current to sternum line 19. As previously described, the pacing current is typically increased by about 5 mA with each successive pacing pulse until the pulses are of sufficient strength to cause the heart muscle to contract. Control circuit 10 (FIG. 4) controls switch SW4 to be turned on for the desired duration of a pacing pulse. Because switch SW4 is implemented with an IGBT in this embodiment (in contrast to the SCR used in FIG. 5), switch SW4 is conductive even for the relatively small currents of the pacing pulses. Thus, as shown in FIG. 9, pulses 96 and 97 of waveform 91 are negative pulses. The embodiment of FIG. 8 advantageously allows for generation of biphasic defibrillation pulses with a positive first phase and negative second phase, while also allowing generation of negative monophasic pacing pulses.

Alternatively, control circuit 10 (FIG. 4) may be configured to adjust the voltage across energy storage capacitor 24 instead of the current provided by current source circuit 50. In this alternative embodiment, control circuit 10 (FIG. 4) would estimate the capacitor voltage required to produce the desired pacing current for the next pacing pulse. In addition, current source circuit 50 would be operated as a switch. Thus, switch driving circuit 71 can be identical to switch driving circuit 52 (FIG. 5). In this alternative embodiment, the value of resistor R4 would be increased to about 500 Ω or greater to provide better current regulation. In another embodiment of this alternative capacitor voltage adjustment technique, current source circuit 50 may be replaced with bypass circuit 40 (FIG. 5) that uses a relatively inexpensive relay circuit instead of a relatively costly IGBT circuit. The differences between the current source regulation technique and this capacitor voltage regulation technique are more clearly set forth in FIG. 11.

Figure 10:
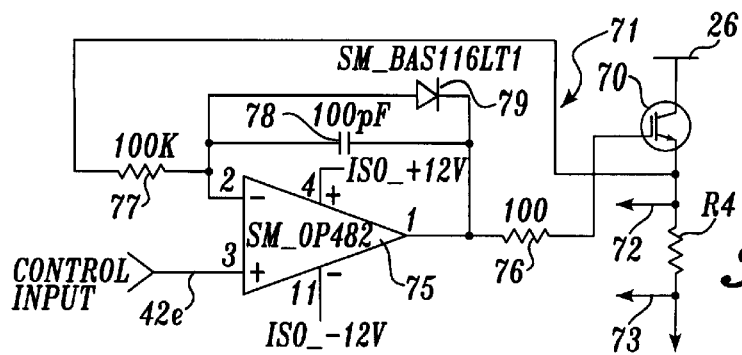
FIG. 10 is a schematic diagram of an IGBT driver for linear control of an IGBT, according to one embodiment of the present invention.

FIG. 10 is a diagram illustrative of one embodiment of IGBT switch driving circuit 71 for biasing an IGBT to operate in the linear region so as to control the current conducted by the IGBT. In this embodiment, switch driving circuit 71 includes an operational amplifier 75, resistors 76 and 77, a capacitor 78 and a diode 79.

Switch driving circuit 71 is interconnected as follows. Operational amplifier 75 has its non-inverting input lead connected to control line 42e. The output lead of operational amplifier 75 is connected to one terminal of resistor 76. The other terminal of resistor 76 is connected to the gate of IGBT 70. Resistor 77 is connected between the inverting input lead of operational amplifier 75 and the drain of IGBT 70. Capacitor 78 and diode 79 are connected between the output lead and the inverting input lead of operational amplifier 75, with diode 79 being connected to allow current to flow from the inverting input lead to the output lead of operational amplifier 75.

Switch driving circuit 71 uses a feedback scheme to control IGBT 70 to operate in the linear region to achieve a desired output current. Control circuit 10 (FIG. 4) monitors the current outputted by IGBT 70 through resistor R4 as previously described and adjusts the voltage level of the control signal at control line 42e to achieve the desired current level. Capacitor 78 causes switch driving circuit 71 to function in a manner similar to an integrator, with its input signal being the voltage at the drain of IGBT 70. Thus, when the voltage level at control line 42e is zero, the output voltage of operational amplifier 75 is also zero, causing IGBT 70 to be non-conductive.

When the voltage at control line 42e is positive relative to the voltage at the inverting input lead of operational amplifier 75, the "integrator" operates to increase the voltage at its output lead, which in turn causes IGBT 70 to be more conductive and pull up the voltage at its drain. Because this drain voltage is fed back to the inverting input lead of operational amplifier 75, the "integrator" only increases its output voltage until the drain voltage is substantially equal to the voltage at the noninverting input lead. That is, the "virtual ground" effect of operational amplifiers causes the "integrator" to quickly drive the drain voltage to be equal to the voltage at control line 42e.

In a symmetrically opposite manner, when the voltage at control line 42e is negative relative to the voltage at the inverting input lead of operational amplifier 75, the "integrator" operates to decrease the voltage at its output lead, which in turn causes IGBT 75 to become less conductive and quickly drive the drain voltage of IGBT 70 to be substantially equal to the voltage at control line 42e. Diode 79 helps to prevent the voltage at the drain of IGBT 70 from being above the voltage at the gate of IGBT 70 by more than a diode threshold voltage.

Thus, when the control circuit 10 (FIG. 4) wishes to increase the output current of IGBT 70, control circuit 10 causes the voltage level at control line 42e to increase. As described above, increasing the voltage at control line 42e causes the output current of IGBT 75 to increase, which is then detected by control circuit 10 (FIG. 4) in monitoring the voltage across resistor R4. When the output current reaches the desired level, control circuit 10 (FIG. 4) can then stop increasing the voltage at control line 42e. Conversely, to decrease the output current of IGBT 70, control circuit 10 (FIG. 4) causes the voltage level at control line 42e to decrease, whereby causing the output current of IGBT 70 to decrease. When the output current reaches the desired level, control circuit 10 (FIG. 4) can then stop decreasing the voltage at control line 42e.

Figure 11:
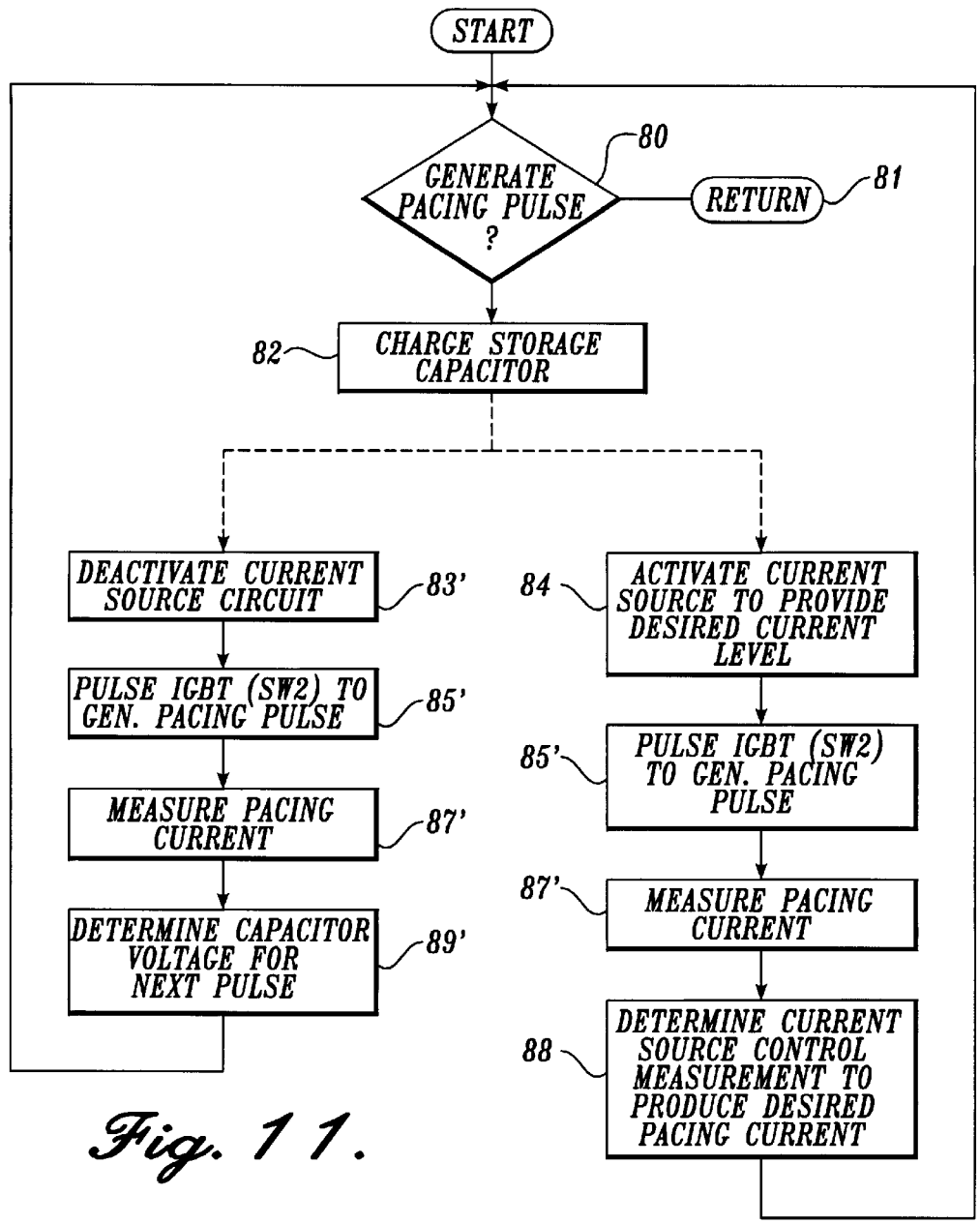
FIG. 11 is a flow diagram illustrative of the operation of the combined defibrillator/pacer unit depicted in FIG. 8.

FIG. 11 is a flow diagram summarizing the operation of the embodiment of FIG. 8 in generating pacing pulses for both capacitor voltage regulation and current source regulation. Steps 80–82 are as described above in conjunction with FIG. 6. In the capacitor voltage regulation technique, control circuit 10 (FIG. 4) performs steps 83', 85', 87' and 89', which are essentially the same as steps 83, 85, 87 and 89 described above in conjunction with FIG. 6 (except that current source circuit 50 is used instead of bypass circuit 40).

In the current regulation technique, following step 82, control circuit 10 (FIG. 4) controls switch driving circuit 71 to activate current source circuit 50 to provide the desired current for the pending pacing pulse in a step 84. Then steps 85' and 87' are performed as in the capacitor voltage regulation technique. In a next step 88, control circuit 10 (FIG. 4) determines the control signal adjustments needed to produce the desired pacing current for the next pulse. As described earlier, the pacing current is typically increased in 5 mA increments until a maximum level is reached.

Figure 12:
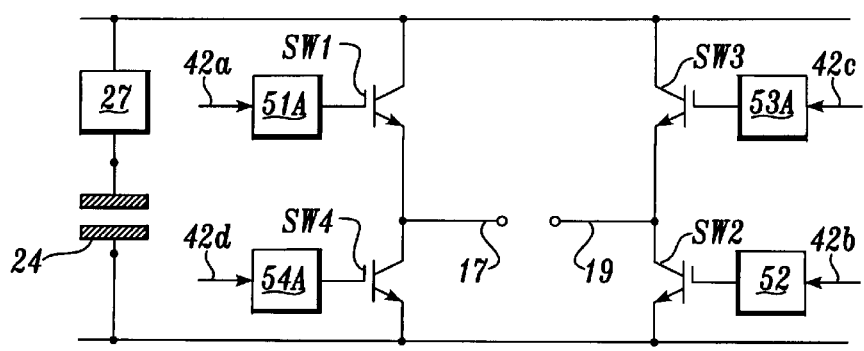
FIG. 12 is a block diagram illustrative of a combined defibrillator/pacer unit, according to yet another embodiment of the present invention.

FIG. 12 is a diagram illustrating an embodiment of H-bridge 14 that has four IGBT legs and no SCR legs that can be advantageously used to generate biphasic pacing and biphasic defibrillation pulses using a constant energy technique. This embodiment is similar to the embodiment of FIG. 8, except that current source circuit 50 is omitted and switches SW1 and SW3 are IGBT switches essentially identical to IGBT switch SW2. In addition, instead of switch driving circuits 51 and 53 (FIG. 5) for SCR switches, this embodiment includes switch driving circuits 51A and 53A that are essentially identical to switch driving circuit 71 (FIG. 10). In particular, switch driving circuits 51A and 53A would include circuitry similar to circuit 71 (FIG. 10) to operate the IGBTs in the linear region to control the pacing current. To generate both defibrillation and pacing pulses, switches SW1–SW4 are turned off and on in the same sequence described above in conjunction with FIG. 8 to generate defibrillation pulses. However, when generating pacing pulses, control circuit 10 (FIG. 4) controls the current level for each subsequent pacing pulse by operating the IGBTs of switches SW1 and SW3 in the linear region. The use of IGBT switches in all of the legs of H-bridge 14 allow conduction of the relatively small currents used in pacing pulses, while withstanding the relatively high current levels used in defibrillation pulses.

To generate a biphasic pulse with a positive first phase and a negative second phase, switches SW1 and SW2 would be turned on during the first phase while switches SW3 and SW4 are turned off. The negative second phase would be generated by turning off switches SW1 and SW2 and turning on switches SW3 and SW4. Conversely, to generate biphasic pulses of the opposite polarity (i.e., with a negative first phase), during the first phase, switches SW3 and SW4 would be turned on while switches SW1 and SW2 are turned off. The positive second phase would be generated by turning on switches SW1 and SW2 and turning off switches SW3 and SW4.

Figure 13:
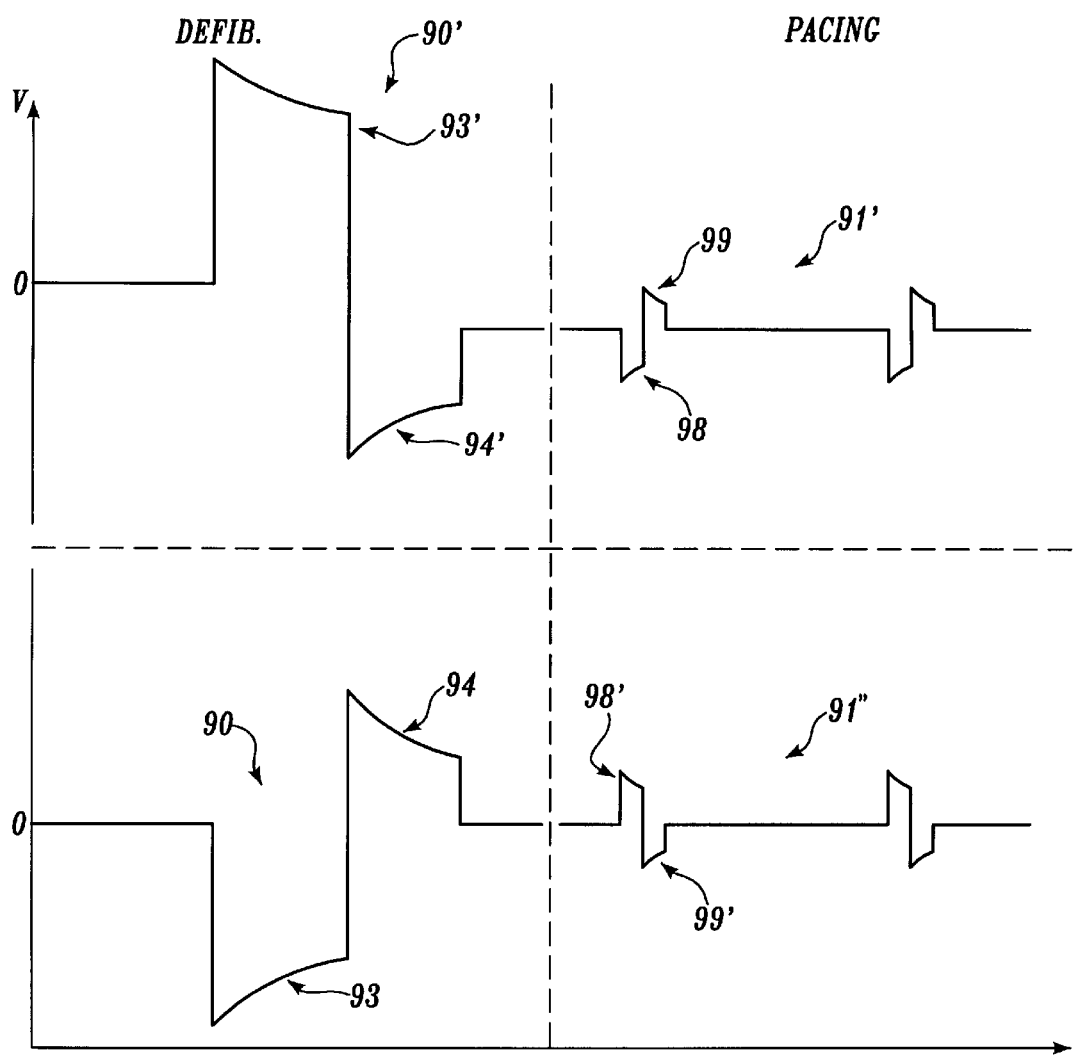
FIG. 13 is a diagram illustrative of various waveforms generated by the combined defibrillator/pacer unit depicted in FIG. 12.

FIG. 13 illustrates two defibrillation waveforms (i.e., waveforms 90 and 90') and two pacing waveforms (i.e., waveforms 91' and 91") that can be generated by using this embodiment of H-bridge 14 (FIG. 12). For example, this embodiment of H-bridge 14 can generate biphasic defibrillation waveform 90' having a positive first phase 93' and a negative second phase 94'. H-bridge 14 (FIG. 12) can also generate biphasic defibrillation waveform 90, which has a negative first phase 93 and a positive second phase 94. H-bridge 14 (FIG. 12) can also generate biphasic pacing waveform 91' in which each of the biphasic pacing pulses has a negative first phase 98 and a positive second phase 99. H-bridge 14 (FIG. 12) can also generate biphasic pacing waveform 91" in which each of the biphasic pacing pulses has a negative first phase 98' and a positive second phase 99'.

Although not illustrated in FIG. 13, those skilled in the art will appreciate that H-bridge 14 (FIG. 12) can also generate monophasic waveforms or even other multiphasic waveforms with appropriate control of switches SW1–SW4. In light of this disclosure, those skilled in the art can, without undue experimentation, provide a suitable software or firmware program that microprocessor 20 of control circuit 10 (FIG. 4) can execute to generate the appropriate switch control signals.

Figure 14:
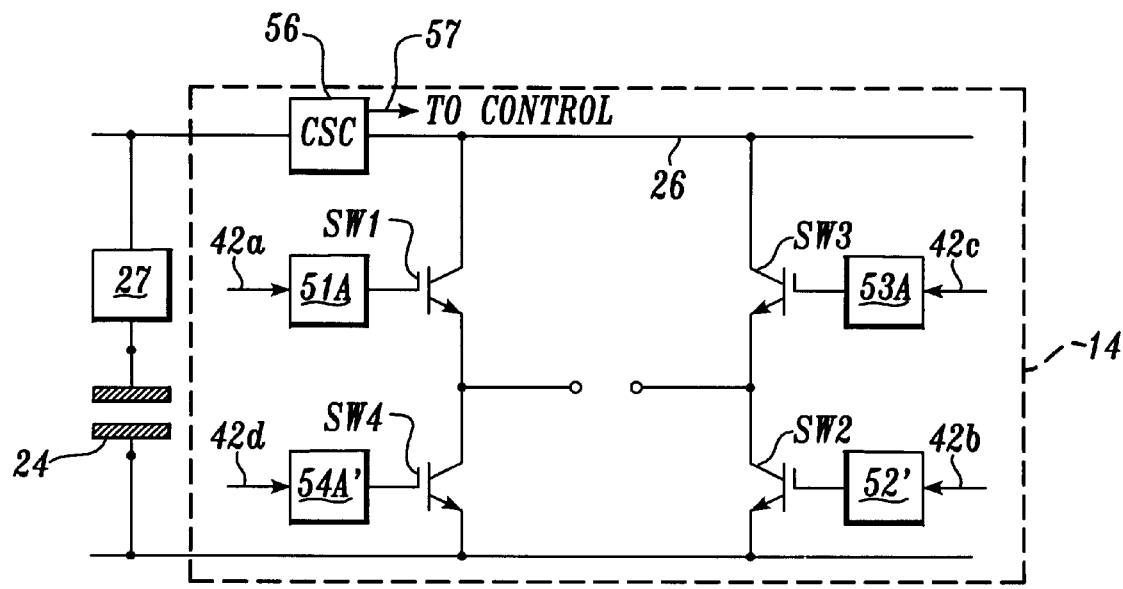
FIG. 14 is a block diagram illustrative of a combined defibrillator/pacer unit, according to still another embodiment of the present invention.

FIG. 14 is a diagram illustrating still another embodiment of H-bridge 14. This embodiment is similar to the embodiment of FIG. 12, except that this embodiment includes a current sensing circuit 56 connected between energy storage capacitor 24 and line 26 that supplies current from energy storage capacitor 24 to switches SW1–SW4. This embodiment is advantageously used to generate constant current pacing pulses by linear operation of switches SW2 and SW4 (or, alternatively, switches SW1 and SW3). Consequently, the switch driving circuits connected to switches SW2 and SW4 (or switches SW1 and SW3 in the alternative embodiment) are essentially identical to switch driving circuit 71 (FIG. 10).

During the defibrillation mode, switches SW1–SW4 are controlled to operate as switches (i.e., not as current sources). To generate a biphasic defibrillation pulse, control circuit 10 (FIG. 4) is configured to turn switches SW1–SW4 off and on as described above for the embodiment of FIG. 12, without regard to the current sensed by current sensing circuit 56.

However, in operation during the pacing mode, current sensing circuit 56 monitors the current flowing from energy storage capacitor 24 to line 26 and generates on a line 57 a current sense signal indicative of the current level. Control circuit 10 (FIG. 4) is connected to line 57 and, based on the detected current level, adjusts the control signals on lines 42d and 42b so that IGBT switches SW2 and SW4 conduct the desired level of current for each phase the pacing pulse. This can be done "on-the-fly" by control circuit 10. Of course, in the alternative embodiment in which switches SW1 and SW3 are operated in the linear region, control circuit 10 (FIG. 4) would adjust the control signal on lines 42a and 42c so that IGBT switches SWI and SW3 conduct the desired level of current for each phase of the pacing pulse.

Figure 15:
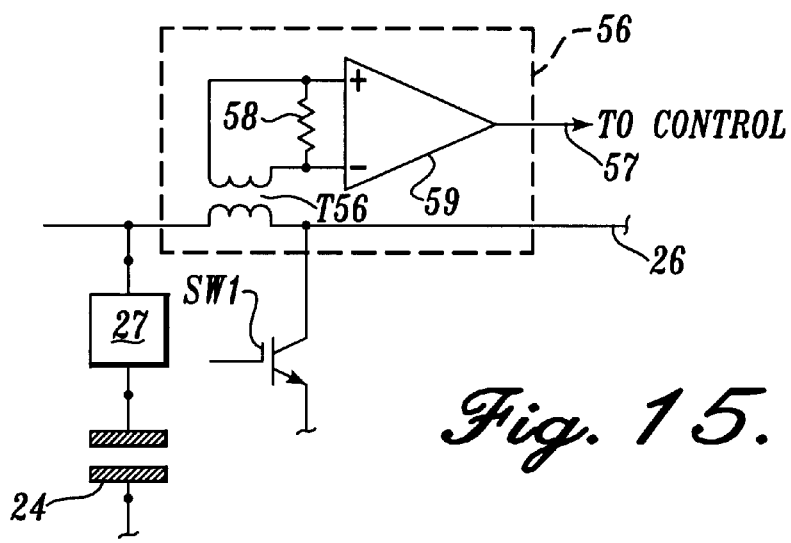
FIG. 15 is a diagram illustrative of current sensing circuit, according to one embodiment of the present invention.

FIG. 15 illustrates one embodiment of current sensing circuit 56. In this embodiment, current sensing circuit 56 includes a transformer T56, a resistor 58 and an amplifier 59. The primary winding of transformer T56 is connected to conduct the current flowing from energy storage capacitor 24 to line 26. Thus, as current flows in the primary winding of transformer T56, a proportional current flows in the secondary winding of transformer T56 and through resistor 58. The input leads of amplifier 59 are connected on either side of resistor 58 so that amplifier 59 will generate on line 57 an output signal having a level that is a function of the voltage drop across resistor 58. Given the known characteristics of amplifier 59 and transformer T56, control circuit 10 (FIG. 4) can generate appropriate control signals to control the current conducted by switches SW2 and SW4 to the desired pacing current levels.

While the preferred embodiment of the invention has been illustrated and described, it will be apparent that various changes can be made therein without departing from the spirit and scope of the invention. For example, control lines 42c and 42d and control switches SW31 and SW41 could be replaced by a single control line and control switch to activate switch driving circuits 53 and 54. Also, while the preferred construction for switches 31, 32, 33, and 34 is described above, it will be appreciated that other switch constructions may be envisioned, such as replacing switch 32 with a single IGBT of sufficient stand-off voltage. Or, additional semiconductor switches may be incorporated in each leg to reduce the voltage that must be switched by each switch. To minimize the size and weight of the resulting H-bridge output circuit, however, the construction described above is preferable. Consequently, within the scope of the appended claims, it will be appreciated that the invention can be practiced otherwise than as specifically described herein. Further, although an H-bridge configuration is described for the energy transfer circuit, other types of energy transfer circuits may be used.

We claim:

1. A circuit that generates a defibrillation pulse in a defibrillation mode and a pacing pulse in a pacing mode, the circuit comprising:

an energy storage capacitor having a first electrode and a second electrode;

a charging circuit coupled to the energy storage capacitor, wherein the charging circuit is configured to charge the energy storage capacitor;

an energy transfer circuit coupled to the energy storage capacitor, the energy transfer circuit having a first output lead and a second output lead, wherein the energy transfer circuit is configured to selectively electrically couple the first and second electrodes of the energy storage capacitor to the first and second output leads; and a control circuit coupled to the charging circuit and the energy transfer circuit, wherein the control circuit is configured to cause the charging circuit to charge the energy storage capacitor to a predetermined level and, when the energy storage capacitor is charged, to control the energy transfer circuit to couple the first and second electrodes of the energy storage capacitor to the first and second output leads of the energy transfer circuit so that the energy transfer circuit provides:

during the defibrillation mode, an external defibrillation pulse at the first and second output leads using energy stored in the energy storage capacitor, and during the pacing mode, an external pacing pulse at the first and second output leads using energy stored in the energy storage capacitor.

2. The circuit of claim 1 wherein the energy transfer circuit comprises four legs, a first leg of the energy transfer circuit including a first IGBT switch circuit and a second, a third and fourth leg of the energy transfer circuit each including an SCR switch circuit.

3. The circuit of claim 2 wherein the energy transfer circuit comprises a bypass circuit, the bypass circuit being coupled in parallel with the third leg of the energy transfer circuit, and wherein the bypass circuit is configured to provide a conductive path that bypasses the third leg of the energy transfer circuit during the pacing mode and is configured to open circuit the conductive path during the defibrillation mode.

4. The circuit of claim 3 wherein the defibrillation pulse is selectably provided as a biphasic pulse and the pacing pulse is provided as a monophasic pulse.

5. The circuit of claim 3 wherein, during the pacing mode, the control circuit is configured to determine the predetermined level in charging the energy storage capacitor to achieve a predetermined current level for a subsequently provided pacing pulse.

6. The circuit of claim 2 wherein the H-bride circuit comprises a current source circuit, the current source circuit being coupled in parallel with the third leg of the energy transfer circuit, and wherein the current source circuit is configured to provide a configurable current to the first output lead during the pacing mode and is configured to provide essentially no current to the first output lead during the defibrillation mode.

7. The circuit of claim 6 wherein, during the pacing mode, the control circuit is configured to cause the current source circuit to provide the configurable current with a predetermined current level.

8. The circuit of claim 6 wherein the current source circuit comprises an IGBT and a resistor.

9. The circuit of claim 1 wherein the energy transfer circuit comprises four legs, a first leg and a second leg of the energy transfer circuit each including an IGBT switch circuit, and a third leg and a fourth leg of the energy transfer circuit each including an SCR switch circuit.

10. The circuit of claim 9 wherein the H-bride circuit comprises a bypass circuit, the bypass circuit being coupled in parallel with the third leg of the energy transfer circuit, and wherein the bypass circuit is configured to provide a conductive path that bypasses the third leg of the energy transfer circuit during the pacing mode and is configured to open circuit the conductive path during the defibrillation mode.

11. The circuit of claim 10 wherein the defibrillation pulse is selectably provided as a biphasic pulse having a first phase with a first polarity and a second phase of a second polarity, and wherein the pacing pulse is provided as a monophasic pulse with the second polarity.

12. The circuit of claim 11 wherein, during the pacing mode, the control circuit is configured to determine the predetermined level in charging the energy storage capacitor to achieve a predetermined current level for a subsequently provided pacing pulse.

13. The circuit of claim 9 wherein the H-bride circuit comprises a current source circuit, the current source circuit being coupled in parallel with the third leg of the energy transfer circuit, and wherein the current source circuit is configured to provide a configurable current to the first output lead during the pacing mode and is configured to provide essentially no current to the first output lead during the defibrillation mode.

14. The circuit of claim 13 wherein, during the pacing mode, the control circuit is configured to cause the current source circuit to provide the configurable current with a predetermined current level.

15. The circuit of claim 13 wherein the current source circuit comprises an IGBT and a resistor.

16. The circuit of claim 13 wherein the current sense circuit comprises an amplifier, a transformer and a resistor.

17. The circuit of claim 1 wherein the energy transfer circuit comprises four legs, each of the four legs of the energy transfer circuit including an IGBT switch circuit.

18. The circuit of claim 17 wherein the defibrillation and pacing pulses are selectably provided as a biphasic pulse or monophasic pulse.

19. The circuit of claim 18 wherein the defibrillation pulse is a biphasic pulse having a first phase with a first polarity and a second phase of a second polarity, and wherein the pacing pulse is a monophasic pulse with the second polarity.

20. The circuit of claim 18 wherein the defibrillation pulse is a biphasic pulse having a first phase with a first polarity and a second phase of a second polarity and the pacing pulse is a biphasic pulse having a first phase of the second polarity and a second phase of the first polarity.

21. The circuit of claim 17 wherein, during the pacing mode, the control circuit is configured to determine the predetermined level in charging the energy storage capacitor to achieve a predetermined current level for a subsequently provided pacing pulse.

22. The circuit of claim 17 wherein the H-bride circuit comprises a current sense circuit coupled to the energy storage capacitor and the control circuit, and wherein the current sense circuit is configured to detect a current level of current provided by the energy storage capacitor when the circuit is providing a pacing pulse.

23. The circuit of claim 22 wherein, during the pacing mode, the control circuit is configured to cause the third and fourth legs of the energy transfer circuit to conduct a predetermined level of current when the circuit is providing a pacing pulse.

24. The circuit of claim 1, wherein the energy transfer circuit is configured as an H-bridge.

25. The circuit of claim 1, wherein the energy storage capacitor is a single capacitor.

26. A method of externally providing a defibrillation pulse or a pacing pulse to a patient from a single unit, the method comprising:
   charging an energy storage capacitor;
   during a defibrillation mode, transferring energy from the energy storage capacitor to the patient in a defibrillation pulse; and
   during a pacing mode, transferring energy from the energy storage capacitor to the patient in a pacing pulse.

27. The method of claim 26 wherein an energy transfer circuit is used to transfer energy from the energy storage capacitor to the patient in both the defibrillation and pacing modes.

28. The method of claim 26 wherein the energy storage capacitor is charged to a predetermined level so that the pacing pulse has a current of a predetermined level.

29. The method of claim 26 wherein the pacing pulse is a biphasic pulse.

30. An apparatus for providing to a patient a defibrillation pulse during a defibrillation mode and a pacing pulse during a pacing mode, the apparatus comprising:
   an energy storage capacitor;
   charging means for charging the energy storage capacitor;
   switch means coupled to the energy storage capacitor for selectively transferring energy from the energy storage capacitor to the patient externally; and
   control means for causing the switch means to transfer energy from the energy storage capacitor to the patient externally in a defibrillation pulse during the defibrillation mode, and for transferring energy from the energy storage capacitor to the patient externally in a pacing pulse during the pacing mode.

31. The apparatus of claim 30 wherein the switch means comprises an energy transfer circuit, wherein the energy transfer circuit is selectively configurable to transfer energy from the energy storage capacitor to the patient in both the defibrillation and pacing modes.

32. The apparatus of claim 30 wherein the control means is configured to cause the charging means to charge the energy storage capacitor to a predetermined level wherein the pacing pulse has a current of a predetermined level.

33. The apparatus of claim 30 wherein the pacing pulse is a biphasic pulse.

* * * * *

UNITED STATES PATENT AND TRADEMARK OFFICE
CERTIFICATE OF CORRECTION

PATENT NO.    : 6,208,895 B1
DATED         : March 27, 2001
INVENTOR(S)   : J.L. Sullivan et al.

It is certified that error appears in the above-identified patent and that said Letters Patent is hereby corrected as shown below:

<u>Title page,</u>
Item [56], References Cited, U.S. PATENT DOCUMENTS, insert in appropriate numerical order the following:

U.S. PATENT DOCUMENTS

| | | |
|---|---|---|
| -- 5,620,465 | 4/1997 | Olson et al. |
| 5,607,454 | 3/1997 | Cameron et al. |
| 5,601,608 | 2/1997 | Mouchawar |
| 5,601,612 | 2/1997 | Gliner et al. |
| 5,593,427 | 1/1997 | Gliner et al. |
| 5,591,209 | 1/1997 | Kroll |
| 5,591,210 | 1/1997 | Kroll et al. |
| 5,591,211 | 1/1997 | Meltzer |
| 5,591,213 | 1/1997 | Morgan |
| 5,534,015 | 7/1996 | Kroll et al. |
| 5,531,765 | 7/1996 | Pless |
| 5,514,160 | 5/1996 | Kroll et al. |
| 5,507,781 | 4/1996 | Kroll et al. |
| 5,470,341 | 11/1995 | Kuehn et al. |
| 5,468,254 | 11/1995 | Hahn et al. |
| 5,441,518 | 8/1995 | Adams et al. |
| 5,431,682 | 7/1995 | Hedberg |
| 5,431,684 | 7/1995 | Archer et al. |
| 5,431,686 | 7/1995 | Kroll et al. |
| 5,376,103 | 12/1994 | Anderson et al. |
| 5,358,512 | 10/1994 | Hoegnelid et al. |
| 5,099,844 | 3/1992 | Faupel |
| 5,083,562 | 1/1992 | de Coriolis et al. |
| 5,048,521 | 9/1991 | Pless et al. |
| 4,850,357 | 7/1989 | Bach, Jr. |
| 4,821,723 | 4/1989 | Baker, Jr. et al. |
| 4,800,883 | 1/1989 | Winstrom |
| 5,441,518 | 8/1995 | Adams et al. |
| 5,522,853 | 6/1996 | Kroll -- |

UNITED STATES PATENT AND TRADEMARK OFFICE
CERTIFICATE OF CORRECTION

PATENT NO. : 6,208,895 B1
DATED : March 27, 2001
INVENTOR(S) : J.L. Sullivan et al.

It is certified that error appears in the above-identified patent and that said Letters Patent is hereby corrected as shown below:

Title page (cont'd),
FOREIGN PATENT DOCUMENTS, insert in appropriate numerical order the following:

-- FOREIGN PATENT DOCUMENTS
| | | |
|---|---|---|
| WO 95/09673 | 4/1995 | (WO) |
| WO 95/05215 | 2/1995 | (WO) |
| WO 94/27674 | 12/1994 | (WO) |
| WO 93/16759 | 9/1993 | (WO) |
| 0 553 864 A2 | 8/1993 | (EP) |
| WO 98/39060 | 9/1998 | (WO) |
| WO 98/39061 | 9/1998 | (WO) -- |

OTHER PUBLICATIONS, insert in appropriate numerical order the following:

-- OTHER PUBLICATIONS
Bardy et al., "Multicenter Comparison of Truncated Biphasic Shocks and Standard Damped Sine Wave Monophasic Shocks for Transthoracic Ventricular Defibrillation," *Circulation*, vol. 94, No. 10, Nov. 15, 1996, pp. 2507-2514.

Bardy et al., "Truncated Biphasic Pulses for Transthoracic Defibrillation," *Circulation*, vol. 91, No. 6, Mar. 15, 1995, pp. 1768-1774.
Cummins et al., Overview, "Ventricular Fibrillation Automatic External Defibrillators, and the United States Food and Drug
Administration: Confrontation Without Comprehension," *Annals of Emergency Medicine*, vol. 26, No. 5, Nov. 1995, pp. 621, 631. --

Column 19,
Line 12, "claim 1," should read -- claim 1 --

Signed and Sealed this

Seventeenth Day of June, 2003

JAMES E. ROGAN
*Director of the United States Patent and Trademark Office*